US00PP24424P3

(12) United States Plant Patent
Harris

(10) Patent No.: US PP24,424 P3
(45) Date of Patent: May 6, 2014

(54) AZALEA PLANT NAMED 'MNIHAR029'

(50) Latin Name: ***Rhododendron* sp.**
Varietal Denomination: MNIHAR029

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 174 days.

(21) Appl. No.: 13/507,050

(22) Filed: May 31, 2012

(65) Prior Publication Data

US 2013/0326779 P1 Dec. 5, 2013

(51) Int. Cl.
*A01H 5/00* (2006.01)

(52) U.S. Cl.
USPC ..... Plt./239

(58) Field of Classification Search
None
See application file for complete search history.

(56) References Cited

U.S. PATENT DOCUMENTS

PP16,248 P2 * 2/2006 Lee ..... Plt./240
PP17,191 P2 * 11/2006 Harris ..... Plt./240

OTHER PUBLICATIONS

Anonymous. Auburn University Azalea Trials at Camp Hill—Harris Azaleas. See 'Dorothy Clark', p. 7. Accessed Dec. 16, 2013.*

* cited by examiner

*Primary Examiner* — Wendy C Haas
(74) *Attorney, Agent, or Firm* — Jondle Plant Sciences Division of Swanson & Bratschun, L.L.C.

(57) ABSTRACT

A new and distinct variety of azalea plant with spring blooming, attractive, showy, single light pink flowers with a dark pink border, easily propagated by semi-hardwood cuttings in late spring through summer, moderate growth rate under normal fertilization and moisture conditions, compact, broadly rounded, slightly spreading, and freely-branching in habit, grows well in containers, thrives in shade or sun and is hardy in Zone 7, is disclosed.

2 Drawing Sheets

Genus and species: *Rhododendron* sp.
Variety denomination: 'MNIHAR029'.

BACKGROUND OF THE NEW PLANT

The present invention is a new and distinct variety of evergreen azalea of the genus *Rhododendron*. This new azalea, hereinafter referred to as 'MNIHAR029', originated from a controlled cross hybridization in 2000 between the female azalea plant 'Grace Freeman' (unpatented) and the male azalea plant 'Amagasa' (unpatented) in a controlled environment in Lawrenceville, Ga. The present invention has a blooming period of mid March until late April. 'MNIHAR029' has a compact, broadly rounded, slightly spreading, freely branching growth habit, and cold hardiness.

The new plant was first propagated via semi-hardwood cuttings in 2004 in Dearing, Ga. and has been asexually reproduced repeatedly by semi-hardwood cuttings in Dearing, Ga. for over 8 years, four generations. 'MNIHAR029' has been found to retain its distinctive characteristics through successive asexual propagations via semi-hardwood cuttings.

Plant Breeder's Rights for this variety have not been applied for. 'MNIHAR029' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring blooming;
2. Attractive, showy, light pink flowers with a dark pink border;
3. Numerous single flowers;
4. Easily propagated by semi-hardwood cuttings in late spring through summer;
5. Moderate growth rate under normal fertilization and moisture conditions;
6. Compact, broadly rounded, slightly spreading, freely branching growth habit;
7. Grows well in containers;
8. Thrives in shade or sun; and
9. Hardy in Zone 7.

DESCRIPTION OF THE PHOTOGRAPHS

This new azalea hybrid variety is illustrated by the accompanying photographs. The colors shown are as true as can be reasonably obtained by conventional photographic means. The photographs are of four-year-old plants grown in filtered shade and full sun in 2011 and 2012 in Dearing, Ga.

DETAILED BOTANICAL DESCRIPTION OF THE NEW PLANT

Figure 1:
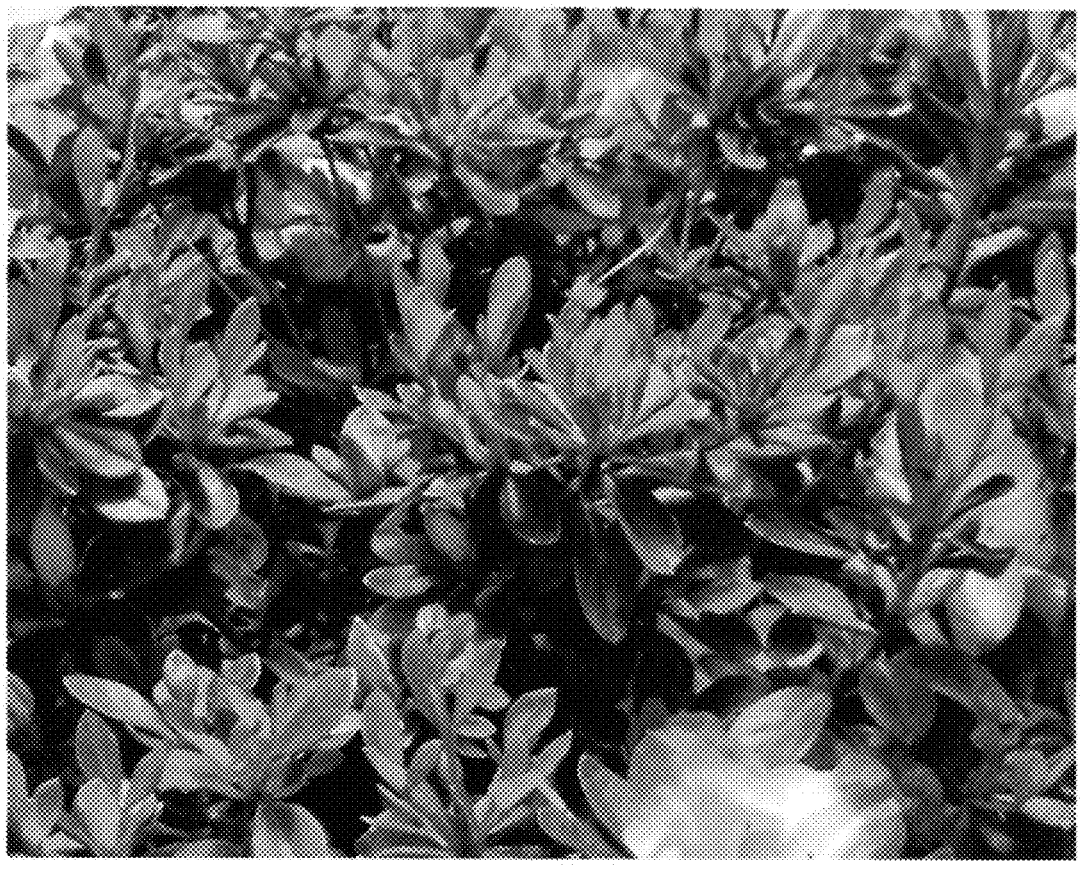
FIG. 1 is a close-up showing flower buds, mature foliage, and immature foliage.
Figure 2:
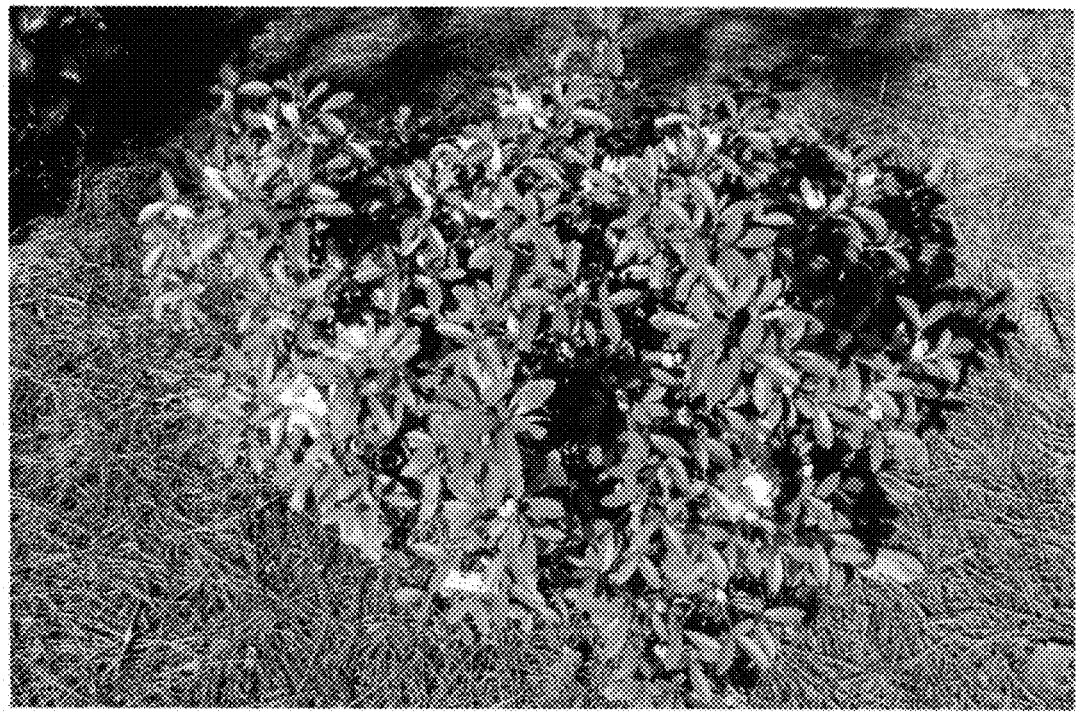
FIG. 2 shows new growth and growth habit.
Figure 3:
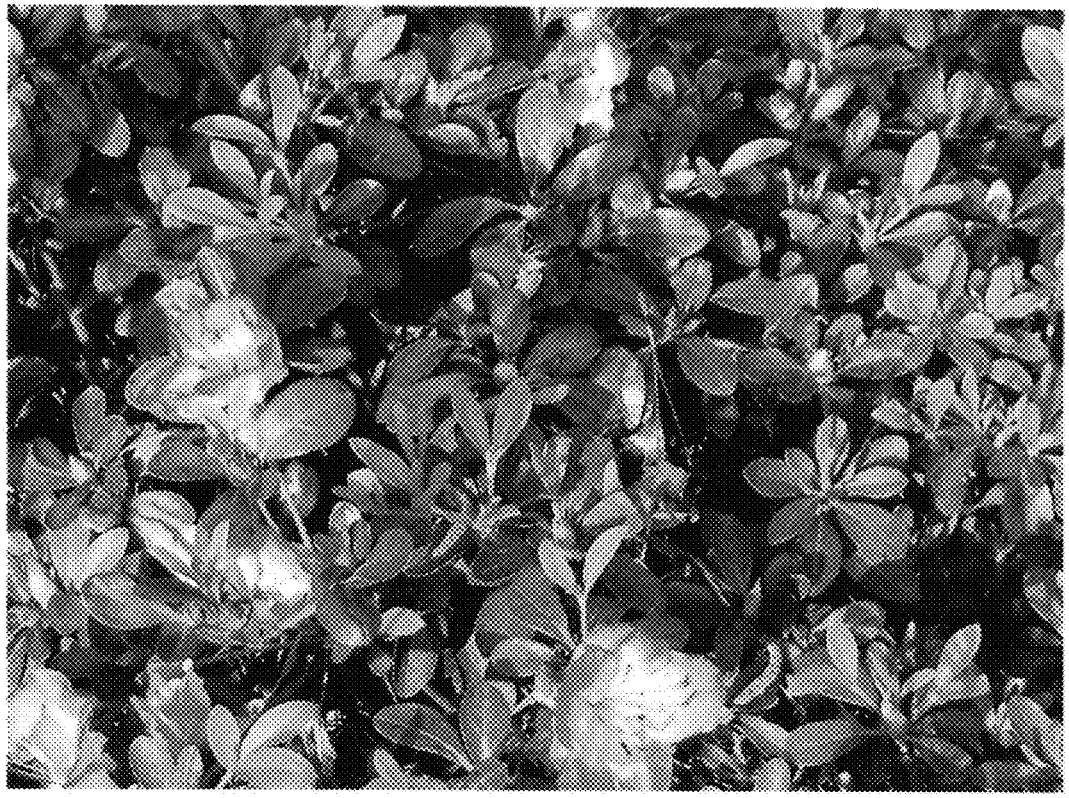
FIG. 3 is a close-up showing flower buds, mature foliage, and new growth.
Figure 4:
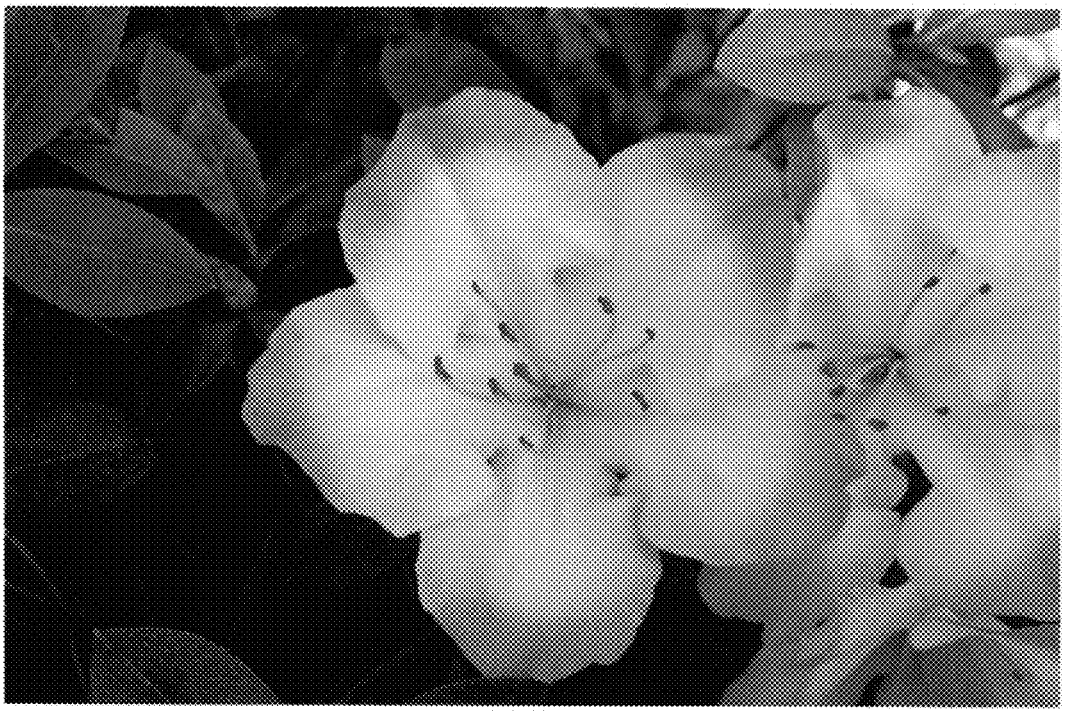
FIG. 4 is a close-up showing flower size, form, and color.

The following is a detailed description of the new variety of azalea based on observations made of two and three-year-old plants grown in trade and three-gallon containers according to wholesale commercial production conditions, under full-sun and six-year-old plants grown in an evaluation bed under semi-shade conditions in Dearing, Ga. in the spring, summer, and fall seasons of 2008, 2009, 2010, 2011, and 2012. The colors of the various plant parts are detailed with reference to The Royal Horticultural Society Colour Chart (2001).

Classification:

*Family.*—Ericaceae.

*Species.*—*Rhododendron* sp.

*Common name.*—Azalea.

*Denomination.*—'MNIHAR029'.

Parentage:

*Female parent.*—The azalea plant 'Grace Freeman' (unpatented).

*Male parent.*—The azalea plant 'Amagasa' (unpatented).

Plant:

*Form.*—Compact, broadly rounded, slightly spreading.

*Texture.*—Medium.

*Height.*—76.2 cm to 91.44 cm.

*Width.*—182.88 cm to 243.84 cm.

*Growth habit.*—Freely branching; compact, broadly rounded, slightly spreading, in nature.

*Growth rate.*—Moderate growth rate under normal fertilization and moisture conditions. In a period of 6 years from a rooted cutting the plant reaches a height of 55.88 cm and a spread of 132.08 cm. The growth rate is normally averages about 13.4 cm per year; the plant reaches a height of 76.2 cm to 91.44 cm at maturity while maintaining a compact, broadly rounded, slightly spreading, habit due to the abundant deliquescent branch development.

*Spring growth.*—The date of initial spring growth is March 20, followed by continuous growth through fall.

*Life cycle.*—Perennial and evergreen.

Leaves:

*Arrangement.*—Alternate, simple, pubescent, and evergreen.

*Shape.*—Elliptical.

*Apex.*—Mucronate.

*Base.*—Attenuate.

*Margin.*—Entire.

*Length.*—3.7 cm.

*Width.*—1.75 cm.

*Venation pattern.*—Pinnate; the mid-veins and laterals are impressed on the upper surface and the prominent on the lower surface. Color: Lower surface: RHS 144B (yellow-green). Upper surface: RHS 144B (yellow-green).

*Immature leaf.*—Upper surface: Color: Matte to semi-glossy, RHS 143A (yellow-green). Pubescence: Strigose. Pubescence color: RHS N155A (white) and RHS 164C (greyed-orange). Lower surface: Color: Matte, RHS 147C (yellow-green). Pubescence: Strigose. Pubescence color: RHS N155A (white) and RHS 164D (greyed-orange).

*Mature leaf.*—Upper surface: Color: Matte, RHS 139A (green). Pubescence: Strigose. Color: RHS 159D (orange-white). Lower surface: Color: Matte, RHS 138B (green). Pubescence: Strigose. Pubescence color: RHS 159A (orange-white).

*Petiole.*—Length: 0.5 cm. Diameter: 0.1 cm by 0.15 cm. Color: Immature: RHS 144C (yellow-green). Mature: RHS 144B (yellow-green). Pubescence: Strigose. Color: Immature: RHS N155A (white) to RHS 164B (greyed-orange). Mature: RHS 164A (greyed-orange).

Stems:

*Form.*—Branched at terminal buds with some from auxiliary buds at leaf nodes.

*Young stems* (*actively growing, less than one year old*).—Color: RHS 144A (yellow-green). Pubescence: Strigose. Pubescence color: Begins RHS N155A (white) and RHS 164D (greyed-orange) maturing to RHS 164A (greyed-orange). Length of fully elongated flush: 5.4 cm on average. Diameter: 0.2 cm.

*Mature stems* (*one year old and older*).—Color: RHS 164A (greyed-orange) and RHS 199B (grey-brown). Pubescence: Strigose, the quantity decreases with age of the stem. Pubescence color: RHS 164A (greyed-orange) and RHS N199B (grey-brown). Length: 14 cm on average for full year's growth. Diameter: 0.35 cm in second year. Pith: Solid and uniform. Internode length: Average 1.0 cm on actively growing vegetative stems.

Flower buds:

*Arrangement and form.*—At terminal; borne in groups of one, two or three, sheathed by one to three modified leaf bracts. Bract length: Average 1.6 cm. Bract Width: 0.5 cm. Bract Color: RHS 147A (yellow-green) and RHS 145A (yellow-green).

*Shape.*—Ovate.

*Apex.*—Acute.

*Base.*—Rounded.

*Length* (*at tight bud*).—1.2 cm.

*Diameter* (*at tight bud*).—0.5 cm.

*Scales.*—Color: Immature: RHS 145C (yellow-green). Mature: RHS 144B (yellow-green) with areas of RHS N34A (orange-red). Length: 1.0 cm. Diameter: 0.7 cm. Texture: Matte; strigillose pubescence. Pubescence color: RHS 159A (orange-white).

*Pedicel.*—Length: 1.1 cm at point bud begins to open. Diameter: 0.2 cm. Texture: Pubescent, sericeous pubescence. Pubescence color: RHS 164A (greyed-orange). Color: RHS 145A (yellow-green) with slight RHS 47A (red) areas near the base of the calyx.

Calyx:

*Sepal length.*—0.5 cm.

*Sepal diameter.*—0.5 cm.

*Calyx diameter.*—0.7 cm from sepal apex to sepal apex.

*Sepal quantity.*—5.

*Texture.*—Pubescent, sericeous pubescence. Pubescence color: RHS 164C (greyed-orange).

*Color.*—RHS 143C (green).

Flowers:

*Type.*—Perfect, single flowers.

*Shape.*—Open funnel-shaped.

*Flowering habit and period.*—Borne on the current season's growth; four weeks beginning mid March and lasting until late April in Dearing, Ga.

*Lastingness of flowers on the plant.*—3 to 6 days in the sun; 3 to 7 days in the shade.

*Fragrance.*—Absent.

*Persistence.*—Self-cleaning.

*Diameter.*—7.2 cm.

*Depth.*—2.6 cm.

*Petals.*—Quantity per flower and arrangement: Five imbricate petals that are fused at the base and remain fused up to 1.6 cm from the base. Shape: Obovate. Apex: Rounded. Base: Fused. Margin: Entire, slightly undulate. Texture (both upper and lower surfaces): Glabrous. Length (of petals): 4.8 cm. Width (of petals): 2.6 cm. Color: Upper surface: RHS 56A (red) with an average of 0.8 cm of RHS 58B (red-purple) at apex, spots are not visible. Lower surface: RHS 56A (red) with an average of 0.8 cm of RHS 58B (red-purple) at apex, spots are not visible.

Reproductive parts:

*Pistil.*—Quantity and form: Single, non-petaloid. Length: 4.8 cm. Diameter: 0.075 cm.

*Stigma.*—Color: RHS 59A (red-purple). Diameter: 0.125 cm.

*Style color.*—RHS 60A (red-purple).

*Ovary.*—Pubescent, pilose RHS N155A (white) with 5 locules.

*Ovary color.*—RHS 141A (green).

*Stamens.*—Quantity: 6 or 9 per flower; non-petaloid. Length: 3.0 cm. Width: 0.075 cm. Color: RHS 49B (red).

*Anther.*—Length: 0.3 cm. Width: 0.1 cm. Color: RHS 164A (greyed-orange). Pollen: Abundant. Color: RHS 158D (yellow-white).

Fruit and seed: Observed.

*Maturity.*—The capsule matures in about 6 months in Dearing, Ga. and the fruit set is moderate and contains about 100 to 200 non-winged seeds.

*Capsule length.*—1.0 cm.

*Capsule width.*—0.8 cm.

*Capsule color.*—RHS 141A (green).

CULTURE

'MNIHAR029' grows well in a wide range of conditions and tolerates sun to shade. 'MNIHAR029' prefers moist, well-drained soil that is rich in organic matter and responds well to mulching and medium applications of fertilizer. 'MNIHAR029' does best in soil with a pH of 5.0 to 5.5 and is propagated with semi-hardwood cuttings in late spring through the summer. Azaleas root in five to six weeks with a high percentage of rooting (80% plus). Tissue culture is also an effective means of propagation for azaleas.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR029' is compared to parental varieties 'Grace Freeman' (unpatented) and 'Amagasa' (unpatented).

TABLE 1

| Characteristic | 'MNIHAR029' | 'Grace Freeman' | 'Amagasa' |
|---|---|---|---|
| Plant Height (Mature) | 76.2 cm to 91.44 cm | 182.88 cm | 91.44 cm |
| Flower Diameter | 7.2 cm | 9.525 cm to 10.16 cm | 7.62 cm to 10.16 cm |
| Flower Form | Single | Single | Single |
| Flower Color | Light pink with a dark pink border | Light Pink | Red |
| Bloom Period | Mid March to late April | April | May |
| Hardy Zone | 7 | 6 | 7 |
| Stamen Number | 6 to 9 | 9 to 10 | 6 to 9 |
| Stamen Type | Non-petaloid | Non-petaloid | Non-petaloid |

When 'MNIHAR029' is compared to the commercial variety 'Roblen' (U.S. Plant Pat. No. 16,248), 'MNIHAR029' has a compact, broadly rounded, slightly spreading growth habit, a height of 55.88 cm and a spread of 132.08 cm in 6 years, while 'Roblen' has a height of 91.44 cm and a spread of 60.96 cm in 6 years. Additionally, 'MNIHAR029' produces single light pink with a dark pink border flowers, while 'Roblen' has single to semi-double bright red flowers.

I claim:

1. A new variety of azalea plant named 'MNIHAR029' as herein shown and described.

* * * * *